(12) United States Patent
Mok et al.

(10) Patent No.: US 9,867,962 B2
(45) Date of Patent: Jan. 16, 2018

(54) DISPLAY APPARATUS, AND DISPLAY CONTROL METHOD AND APPARATUS OF THE DISPLAY APPARATUS

(71) Applicant: Samsung Display Co., Ltd., Yongin (KR)

(72) Inventors: Rangkyun Mok, Yongin (KR); Jongin Baek, Yongin (KR); Wonsang Park, Yongin (KR); Yijoon Ahn, Yongin (KR); Byeonghee Won, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 159 days.

(21) Appl. No.: 14/711,218

(22) Filed: May 13, 2015

(65) Prior Publication Data
US 2016/0129218 A1    May 12, 2016

(30) Foreign Application Priority Data
Nov. 10, 2014   (KR) ........................ 10-2014-0155517

(51) Int. Cl.
  *G09G 5/02*      (2006.01)
  *A61M 21/02*     (2006.01)
  (Continued)

(52) U.S. Cl.
  CPC .......... *A61M 21/02* (2013.01); *A61B 5/4809* (2013.01); *A61M 21/00* (2013.01); *G09G 3/20* (2013.01);
  (Continued)

(58) Field of Classification Search
  CPC ........ A61M 2230/00; A61M 2230/005; A61M 2021/0044; A61M 2021/0083;
  (Continued)

(56) References Cited

U.S. PATENT DOCUMENTS 5,167,228 A * 12/1992 Czeisler ................ A61M 21/00
                                                      607/88
5,304,212 A *  4/1994 Czeisler ................ A61M 21/00
                                                      607/88
(Continued)

FOREIGN PATENT DOCUMENTS

CN         101984487       3/2011
KR      10-2006-0063334    12/2006
(Continued)

*Primary Examiner* — Michael J Jansen, II
(74) *Attorney, Agent, or Firm* — H.C. Park & Associates, PLC (57) ABSTRACT

A display control method for controlling display of a display panel, the display control method including: obtaining an image by photographing a viewer; determining whether the viewer is sleepy based on the image; controlling a display mode of the display panel based on whether the viewer is sleepy; and generating an output signal for displaying an image on the display panel based on the display mode, wherein the display panel includes a first blue pixel emitting a first blue light and a second blue pixel emitting a second blue light having a different wavelength from the first blue light, and the display mode is classified based on which of the first and second blue pixels are used.

15 Claims, 11 Drawing Sheets (51) Int. Cl.
  *A61M 21/00* (2006.01)
  *A61B 5/00* (2006.01)
  *G09G 3/20* (2006.01)
  *A61B 5/18* (2006.01)

(52) U.S. Cl.
  CPC ........ *A61B 5/18* (2013.01); *A61M 2021/0044* (2013.01); *A61M 2021/0083* (2013.01); *A61M 2205/3306* (2013.01); *A61M 2230/00* (2013.01); *G09G 2300/0452* (2013.01); *G09G 2354/00* (2013.01)

(58) Field of Classification Search
  CPC .................. A61M 21/00; A61M 21/02; A61M 2205/3306; A61B 5/18; A61B 5/4809; G09G 2300/0452; G09G 2354/00; G09G 3/20
  See application file for complete search history.

(56) References Cited

U.S. PATENT DOCUMENTS

| | | | | |
|---|---|---|---|---|
| 6,053,936 A * | 4/2000 | Koyama | A61M 21/00 600/27 |
| 6,579,233 B2 * | 6/2003 | Hursh | A61B 5/4809 128/920 |
| 6,690,351 B1 * | 2/2004 | Wong | G06F 1/163 345/156 |
| 7,207,938 B2 * | 4/2007 | Hursh | A61B 5/4809 128/920 |
| 7,710,388 B2 * | 5/2010 | Hirata | G09G 3/2003 345/103 |
| 8,184,132 B2 * | 5/2012 | Sakamoto | G06F 3/011 345/156 |
| 8,643,680 B2 * | 2/2014 | Baldwin | G06F 3/013 345/156 |
| 8,680,518 B2 * | 3/2014 | Kim | H01L 27/3213 257/40 |
| 8,743,099 B2 * | 6/2014 | Lin | G09G 5/00 345/102 |
| 8,810,413 B2 * | 8/2014 | Wong | G06F 3/011 340/573.1 |
| 8,957,847 B1 * | 2/2015 | Karakotsios | G06F 3/013 345/156 |
| 9,024,982 B2 * | 5/2015 | Higashi | G09G 3/3426 345/204 |
| 9,035,980 B2 * | 5/2015 | Yang | G09G 3/3225 345/694 |
| 9,094,539 B1 * | 7/2015 | Noble | H04N 7/00 |
| 9,245,479 B2 * | 1/2016 | Park | G09G 3/3233 |
| 9,406,277 B1 * | 8/2016 | Letourneur | G09G 5/10 |
| 2002/0008696 A1 * | 1/2002 | Wagner | G09G 3/3406 345/204 |
| 2005/0168423 A1 * | 8/2005 | Hirata | G09G 3/2003 345/88 |
| 2005/0177031 A1 * | 8/2005 | Hursh | A61B 5/4809 600/300 |
| 2006/0152525 A1 * | 7/2006 | Woog | G09G 5/003 345/589 |
| 2008/0117323 A1 * | 5/2008 | Sakamoto | G06F 3/011 348/333.01 |
| 2008/0224968 A1 * | 9/2008 | Kashiwabara | G09G 3/2003 345/83 |
| 2009/0172430 A1 * | 7/2009 | Takenouchi | G06F 1/3203 713/310 |
| 2009/0278828 A1 * | 11/2009 | Fletcher | G06F 1/3203 345/207 |
| 2009/0281604 A1 * | 11/2009 | De Boer | A61M 21/00 607/88 |
| 2009/0287433 A1 * | 11/2009 | Houston | G01R 22/10 702/62 |
| 2010/0264850 A1 * | 10/2010 | Yamamoto | G09G 5/14 315/312 |
| 2011/0037781 A1 * | 2/2011 | Kangas | G09G 3/3406 345/690 |
| 2011/0080421 A1 * | 4/2011 | Capener | G09G 5/10 345/589 |
| 2011/0185205 A1 * | 7/2011 | You | G06F 1/3203 713/320 |
| 2011/0227966 A1 * | 9/2011 | Mori | G09G 3/20 345/690 |
| 2011/0260958 A1 * | 10/2011 | Shabel | G06F 1/3203 345/102 |
| 2011/0261308 A1 * | 10/2011 | Kurokawa | G02F 1/13338 349/138 |
| 2012/0092172 A1 * | 4/2012 | Wong | G06F 3/011 340/575 |
| 2012/0105517 A1 * | 5/2012 | Yang | G09G 3/003 345/694 |
| 2012/0147065 A1 * | 6/2012 | Byun | G09G 3/3208 345/690 |
| 2012/0218282 A1 * | 8/2012 | Choboter | G09G 5/00 345/589 |
| 2012/0256967 A1 * | 10/2012 | Baldwin | G06F 3/013 345/684 |
| 2013/0070006 A1 * | 3/2013 | Yang | G09G 3/3225 345/694 |
| 2013/0073449 A1 * | 3/2013 | Voynow | G06Q 30/0601 705/39 |
| 2013/0082991 A1 * | 4/2013 | Lin | G09G 5/00 345/207 |
| 2013/0105778 A1 * | 5/2013 | Kim | H01L 27/3213 257/40 |
| 2013/0169543 A1 * | 7/2013 | Xia | G09G 3/003 345/169 |
| 2014/0063853 A1 * | 3/2014 | Nichol | G02B 6/0028 362/616 |
| 2014/0208145 A1 * | 7/2014 | Piccolotto | G06F 1/32 713/324 |
| 2014/0347410 A1 * | 11/2014 | Higashi | G09G 3/3426 345/695 |
| 2015/0009194 A1 * | 1/2015 | Kim | G09G 3/3233 345/211 |
| 2015/0009242 A1 * | 1/2015 | Park | G09G 3/3233 345/690 |
| 2015/0212575 A1 * | 7/2015 | Song | G06F 3/005 345/156 |
| 2015/0248855 A1 * | 9/2015 | Kim | G09G 3/2074 345/590 |
| 2015/0332628 A1 * | 11/2015 | Ren | G09G 3/3258 345/690 |
| 2015/0340012 A1 * | 11/2015 | Lee | G09G 5/02 345/589 |
| 2015/0348468 A1 * | 12/2015 | Chen | G09G 3/3406 345/207 |
| 2015/0371605 A1 * | 12/2015 | Wu | G09G 5/02 345/604 |
| 2016/0129218 A1 * | 5/2016 | Mok | A61M 21/02 345/694 |
| 2016/0180780 A1 * | 6/2016 | Chen | G09G 3/2003 345/207 |
| 2016/0189670 A1 * | 6/2016 | Kim | G09G 5/02 345/690 |
| 2016/0293139 A1 * | 10/2016 | Kwon | G09G 5/02 |

FOREIGN PATENT DOCUMENTS

| | | |
|---|---|---|
| KR | 10-2007-0083314 | 8/2007 |
| KR | 10-2011-0131913 | 12/2011 |
| KR | 10-2013-0129707 | 11/2013 |

* cited by examiner

DISPLAY APPARATUS, AND DISPLAY CONTROL METHOD AND APPARATUS OF THE DISPLAY APPARATUS

CROSS-REFERENCE TO RELATED APPLICATION

This application claims priority from and the benefit of Korean Patent Application No. 10-2014-0155517, filed on Nov. 10, 2014, which is hereby incorporated by reference for all purposes as if fully set forth herein.

BACKGROUND

Field

Exemplary embodiments relate to a display control method, a display control apparatus, and non-transitory media storing executable instructions for performing a display control method.

Discussion of the Background

Melatonin from among hormones secreted from the body of a person operates as a biological clock. At night, melatonin is secreted to all parts of the body to notify each body part that it is night. When melatonin is secreted, sleep is induced.

When morning comes and light shines, the secretion of melatonin is suppressed and the person wakes up. In detail, it is known that the secretion of melatonin is suppressed when the body recognizes a wavelength of light of about 464 nm. In other words, the body knows when it is night and day based on the wavelength of light of about 464 nm. Generally, people recognize light having a center wavelength of about 470 nm to be blue, and thus, light having a wavelength of about 464 nm may be understood to be blue light.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a display apparatus, and a display control method and apparatus of the display apparatus. In detail, one or more exemplary embodiments include a display apparatus having a wake-up or deep sleep inducing effect, and a display control method and apparatus of the display apparatus.

Additional aspects will be set forth in part in the description which follows and, in part, will be apparent from the disclosure, or may be learned by practice of the inventive concept.

An exemplary embodiment of the present invention discloses a display control method for controlling display of a display panel, the display control method includes: obtaining an image by photographing a viewer; determining whether the viewer is sleepy based on the image; controlling a display mode of the display panel based on whether the viewer is sleepy; and generating an output signal for displaying an image on the display panel based on the display mode, wherein the display panel includes a first blue pixel emitting a first blue light and a second blue pixel emitting a second blue light having a different wavelength from the first blue light, and the display mode is classified based on which one of the first and second blue pixels is used.

An exemplary embodiment also discloses a display control apparatus for controlling display of a display panel, the display control apparatus includes: an image obtainer that obtains an image by photographing a viewer; a sleepiness determiner that determines whether the viewer is sleepy based on the image; a mode controller that controls a display mode of the display panel based on whether the viewer is sleepy; and an output signal generator that generates an output signal for displaying an image on the display panel based on the display mode, wherein the display panel includes a first blue pixel emitting a first blue light and a second blue pixel emitting a second blue light having a different wavelength from the first blue light, and the display mode is classified based on which one of the first and second blue pixels is used.

These general and specific embodiments may be implemented by using a system, a method, a computer program, or a combination of the system, the method, and the computer program.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

In the following description, for the purposes of explanation, numerous specific details are set forth in order to provide a thorough understanding of various exemplary embodiments. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments.

In the accompanying figures, the size and relative sizes of layers, films, panels, regions, etc., may be exaggerated for clarity and descriptive purposes. Also, like reference numerals denote like elements.

When an element or layer is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. Like numbers refer to like elements throughout. As used herein, the term "and/or" includes any and all combinations of one or more of the associated listed items.

Although the terms first, second, etc. may be used herein to describe various elements, components, regions, layers, and/or sections, these elements, components, regions, layers, and/or sections should not be limited by these terms. These terms are used to distinguish one element, component, region, layer, and/or section from another element, component, region, layer, and/or section. Thus, a first element, component, region, layer, and/or section discussed below could be termed a second element, component, region, layer, and/or section without departing from the teachings of the present disclosure.

Spatially relative terms, such as "beneath," "below," "lower," "above," "upper," and the like, may be used herein for descriptive purposes, and, thereby, to describe one element or feature's relationship to another element(s) or feature(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof.

Figure 1:
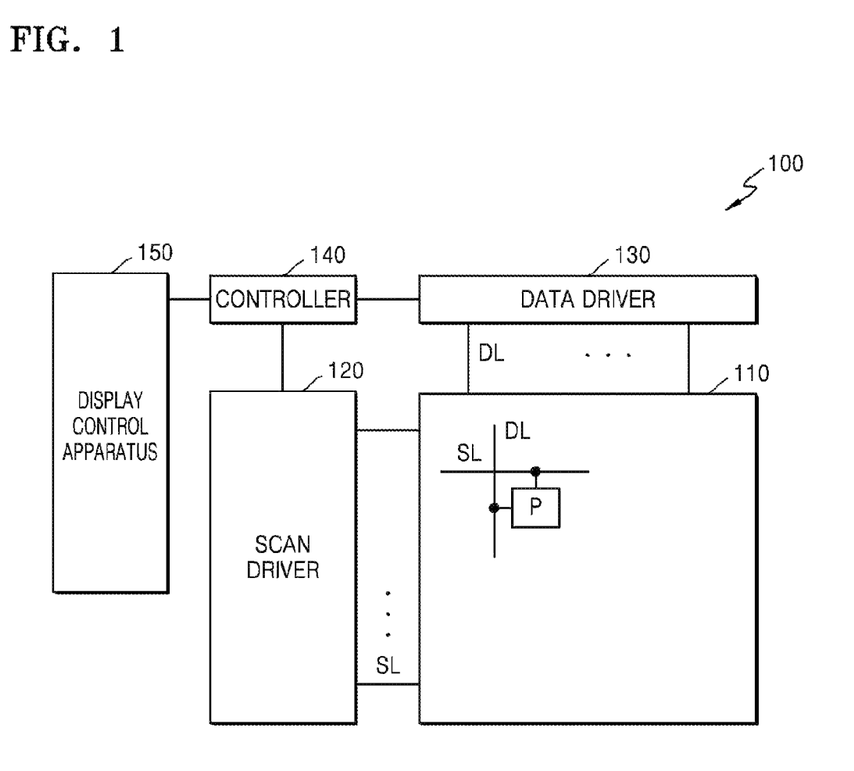
FIG. 1 is a diagram of a display apparatus according to an exemplary embodiment.

FIG. 1 is a diagram of a display apparatus 100 according to an exemplary embodiment.

Referring to FIG. 1, the display apparatus 100 according to an embodiment includes a display panel 110, a scan driver 120, a data driver 130, a controller 140, and a display control apparatus 150.

The display panel 110 may include pixels P, scan lines SL, and data lines DL, and may further include power supply wires (not shown). The pixels P of the display panel 110 are arranged in a matrix form in columns and rows. Each of the data lines DL is connected to the pixels P on the same column and transmits a data signal to the pixels P on the same column. Each of the scan lines SL is connected to the pixels P on the same row and transmits a scan signal to the pixels P on the same row.

The pixel P may include a pixel circuit and a light-emitting device connected to the pixel circuit.

The controller 140 receives an output signal from the display control apparatus 150 and controls the scan driver 120 and the data driver 130. The controller 140 generates a plurality of control signals and digital data. The controller 140 provides a first control signal to the scan driver 120, and provides a second control signal along with digital data to the data driver 130.

In response to the first control signal, the scan driver 120 drives the scan lines SL according to a pre-set order. The scan driver 120 may generate a scan signal and provide the scan signal to the pixels P through the scan lines SL.

In response to the second control signal and the digital data, the data driver 130 drives the data lines DL. The data driver 130 may generate a data signal corresponding to each of the data lines DL and provide the data signals to the pixels P through the data lines DL.

The display control apparatus 150 controls overall display of the display apparatus 100. According to an exemplary embodiment, the display control apparatus 150 may set a display mode of the display apparatus 100, generate an output signal according to the display mode, and transmit the output signal to the controller 140.

The display apparatus 100 may provide a function of waking up a viewer or a function of not interfering with the sleep of the viewer. It is known that the secretion of melatonin is suppressed when the body of a person recognizes a wavelength of light of about 464 nm. Melatonin is a hormone that induces sleep. A display apparatus displays an image by using a plurality of sub-pixels emitting different colors of light, and for example, the display apparatus may include sub-pixels emitting red, green, and blue light, respectively. Here, the blue light contains light having a wavelength of about 464 nm, and thus, when a person is viewing the display apparatus, the secretion of melatonin is suppressed and the display apparatus interferes with the sleep of the person.

The display apparatus 100 includes two types of blue sub-pixels having different center wavelengths. For example, the display apparatus 100 according to an exemplary embodiment may include a first blue pixel emitting a first blue light having a center wavelength that is far from 464 nm, and a second blue pixel emitting a second blue light having a center wavelength that is close to 464 nm. For example, the first blue pixel may emit a dark blue light and the second blue pixel may emit a bright blue (cyan blue) light. The center wavelength of the first blue light may be shorter than that of the second blue light. The center wavelength of the first blue light may be in a range from 440 nm to about 450 nm, and the center wavelength of the second blue light may be in the range from about 460 nm to about 470 nm. For example, the first and second blue pixels may be formed such that the center wavelength of the first blue light is 450 nm and the center wavelength of the second blue light is 464 nm.

When the center wavelength of the first blue light emitted from the first blue pixel is far from 464 nm, melatonin secretion will not be significantly suppressed. However, when the center wavelength of the second blue light emitted from the second blue pixel is close to 464 nm, the secretion of melatonin can be suppressed. Accordingly, the first blue light emitted from the first blue pixel does not interfere with the sleep of the viewer. As a result, sleep is induced. The second blue light emitted from the second blue pixel wakes up the viewer. The display apparatus 100 according to an exemplary embodiment suitably drives the first and second blue pixels according to a desired display mode, thereby providing either a wake-up effect or a sleep inducing effect to the viewer.

A structure of a pixel and a method of driving the pixel, according to one or more exemplary embodiments, will now be described.

FIG. 2A, FIG. 2B, FIG. 2C, and FIG. 2D are schematic diagrams of structures of the pixels P according to exemplary embodiments.

Figure 2A:
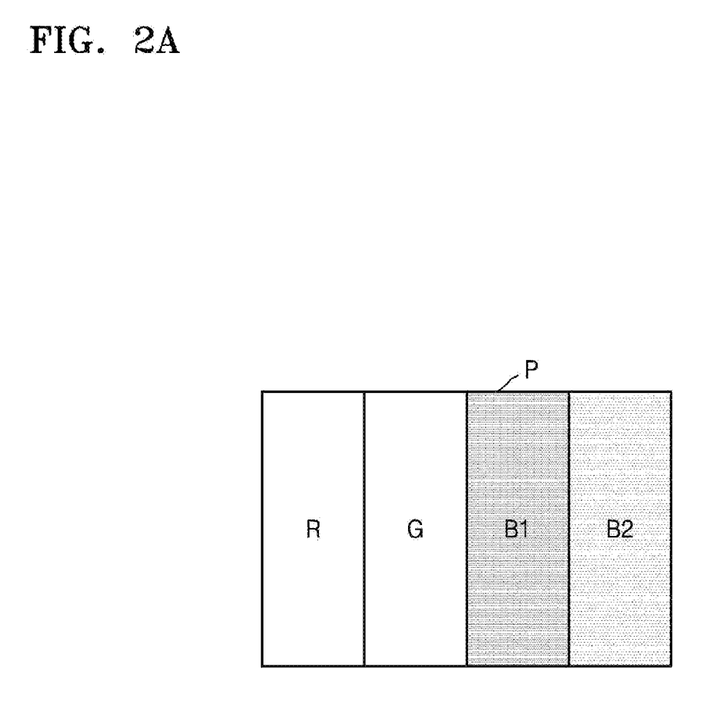
FIG. 2A, FIG. 2B, FIG. 2C, and FIG. 2D are schematic diagrams of structures of pixels according to exemplary embodiments.
Figure 2B:
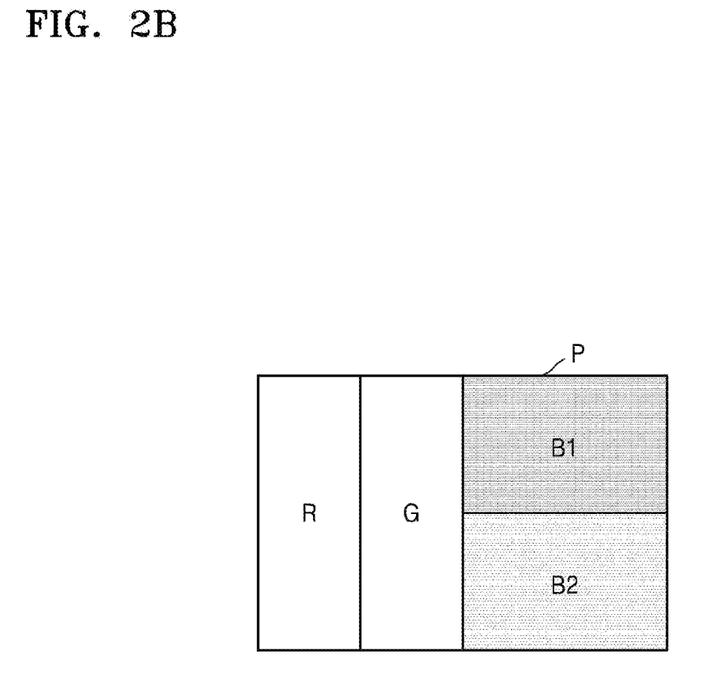
Figure 2C:
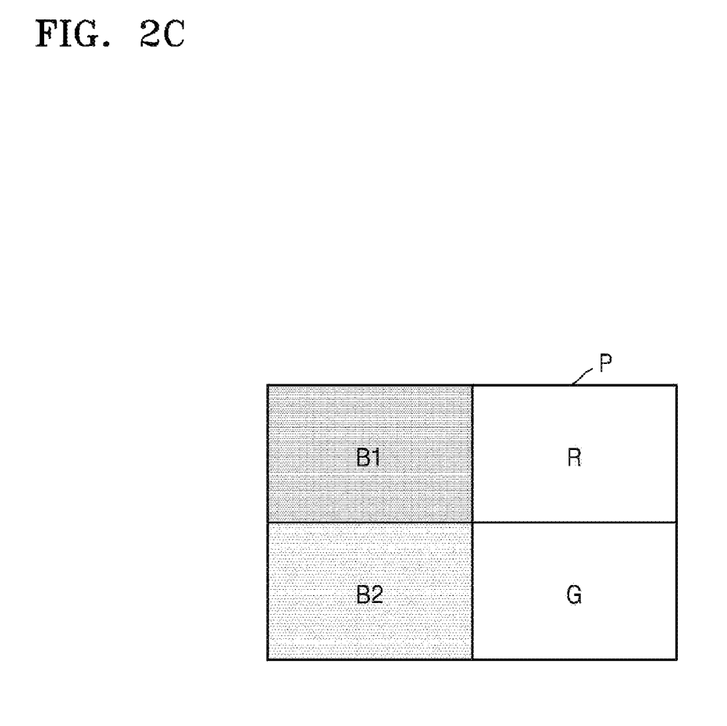

First, referring to FIG. 2A, FIG. 2B, and FIG. 2C, the pixel P included in the display panel 110 may include a plurality of sub-pixels. The pixel P may include two blue sub-pixels and other sub-pixels. For example, as shown in FIGS. 2A through 2C, the pixel P may include a red sub-pixel R, a green sub-pixel G, a first blue sub-pixel B1, and a second blue sub-pixel B2.

Sub-pixels may be arranged in a stripe form, and sub-pixels having different colors may be arranged in vertical stripes, as shown in FIG. 2A. Alternatively, as shown in FIG. 2B, the first and second blue sub-pixels B1 and B2 may be arranged as horizontal stripes. The sub-pixels may also be arranged in a lattice form, as shown in FIG. 2C.

Figure 2D:
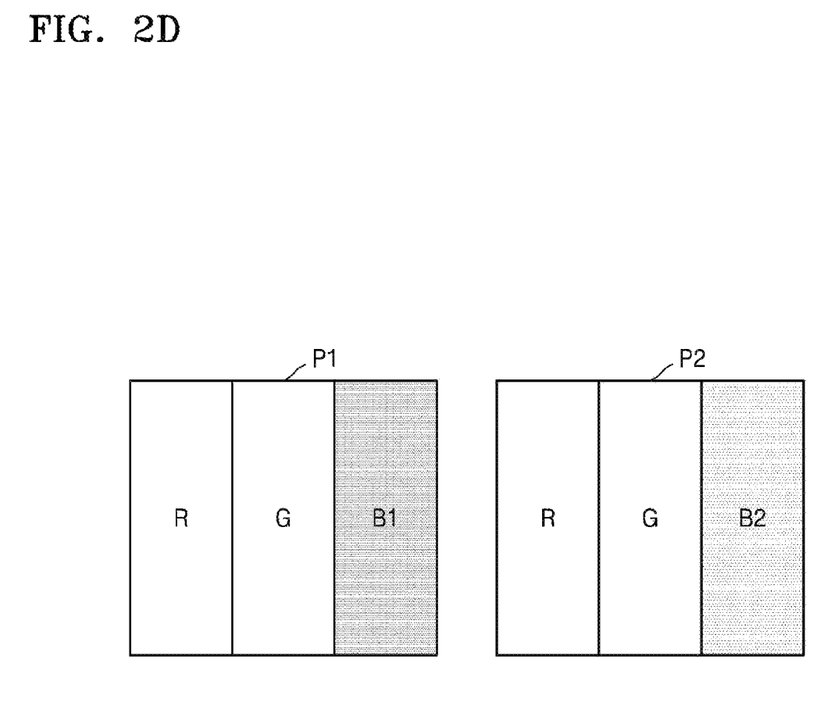

Referring to FIG. 2D, the display panel 110 may include two types of pixels P. For example, the display panel 110 may include a first pixel P1 including the first blue sub-pixel B1 and a second pixel P2 including the second blue sub-pixel B2. The first pixel P1 may include the red sub-pixel R, the green sub-pixel G, and the first blue sub-pixel B1, and the second pixel P2 may include the red sub-pixel R, the green sub-pixel G, and the second blue sub-pixel B2.

Figure 3:
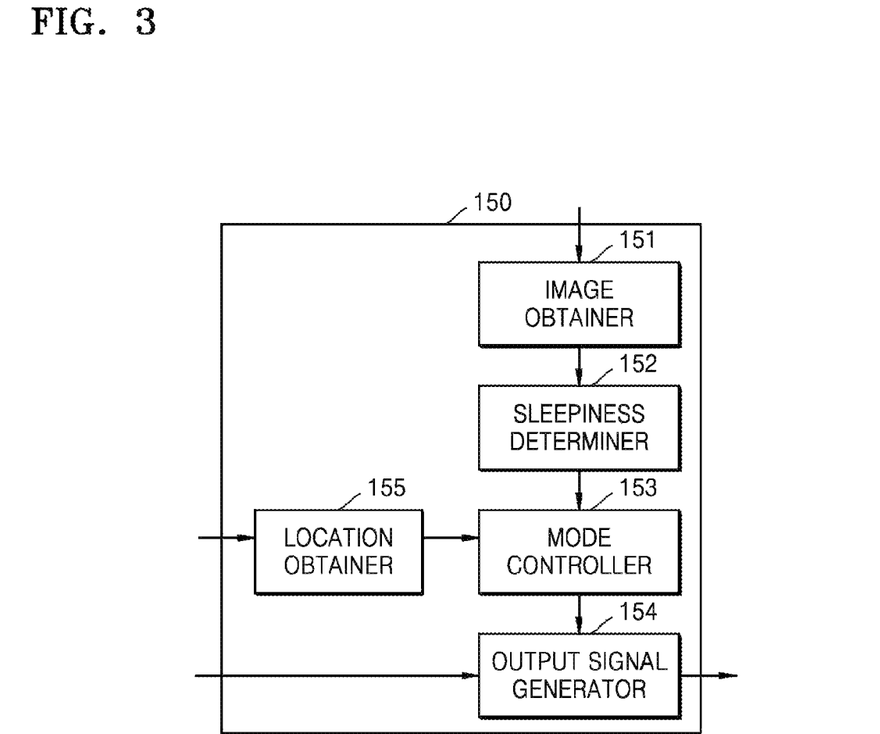
FIG. 3 is a block diagram of a display control apparatus according to an exemplary embodiment.

FIG. 3 is a block diagram of the display control apparatus 150 according to an exemplary embodiment.

In FIG. 3, only essential components of the display control apparatus 150 are shown for convenience of description. In addition to the components shown in FIG. 3, the display control apparatus 150 may include other general-purpose components.

The display control apparatus 150 according to this exemplary embodiment may correspond to at least one processor, or may include at least one processor. Accordingly, the display control apparatus 150 may be driven while being included in another hardware apparatus, such as a microprocessor or a general-purpose computer system.

Referring to FIG. 3, the display control apparatus 150 according to an exemplary embodiment includes an image obtainer 151, a sleepiness determiner 152, a mode controller 153, and an output signal generator 154. The display control apparatus 150 according to an exemplary embodiment may further include a location obtainer 155.

The image obtainer 151 obtains an image by photographing a viewer. Here, the viewer is a person watching the display panel 110, and the image obtainer 151 may obtain the image by photographing the viewer by using a camera that is integrally or separately provided with the display panel 110.

The sleepiness determiner 152 analyzes the image obtained by the image obtainer 151 and determines whether the viewer is sleepy based on the image. The sleepiness determiner 152 determines whether the eyes of the viewer are closed, and when the duration of the eyes being closed is higher than a pre-set reference value, determines that the viewer is sleepy.

The mode controller 153 controls a display mode of the display panel 110 based on whether the viewer is sleepy. The display mode may be controlled by selecting any one of a plurality of display modes classified based on which one of the first and second blue pixels is used. The display modes may include a first mode displaying an image by using the first blue pixel, a second mode displaying an image by using the second blue pixel, and a third mode displaying an image by using both the first and second blue pixels. The mode controller 153 may select any one of the first to third modes as the display mode of the display panel 110.

When it is assumed that a wavelength of the first blue light is shorter than that of the second blue light, the first mode may be a sleep inducing mode, the second mode may be a wake-up mode, and the third mode may be a general mode. When it is determined that the viewer is sleepy, the mode controller 153 may select the second mode to wake up the viewer, and when not, the mode controller 153 may select the third mode. Since the first mode has a sleep inducing effect, the first mode may be selected less than the second and third modes. However, the first mode may be selected to induce the viewer to sleep.

For example, when the viewer is viewing the display panel 110 at night before going to bed, it may be desirable that the display panel 110 not interfere with the sleep of the viewer. Thus, the mode controller 153 may select the first mode at night to induce the viewer to sleep. Alternatively, when the viewer is a driver and the display apparatus 100 is installed in a car, the mode controller 153 may select the first mode when it is nighttime and at the same time immediately before the driver reaches a destination so that the driver may be induced to sleep after reaching the destination.

The mode controller 153 may consider various factors, and for example, may set a display mode by taking into account a pre-set display mode changing cycle, external illuminance, or a current time. For example, when external illuminance is high, the mode controller 153 determines that it is day and selects the second or third mode, and when external illuminance is low, the mode controller 153 determines that it is night and selects the first mode so as not to interfere with the sleep of the viewer. Alternatively, during the day, the mode controller 153 may select the second or third mode, and during the night, the mode controller 153 may select the first mode.

The location obtainer 155 may obtain a current location of the display panel 110. The mode controller 153 may control a display mode by taking into account the current location obtained by the location obtainer 155. For example, when a current location is within a pre-set certain radius from the house of a driver and the current location is gradually approaching the house, the mode controller 153 may select the first mode. Accordingly, the display panel 110 may be driven in the first mode so that the driver is induced to sleep after reaching the house.

The location obtainer 155 may generate a moving path by using information about a departure and a destination and provide a navigating service regarding the moving path. The location obtainer 155 may generate a path by using the departure and the destination, divide the path into first, second, and third sections in the stated order, and provide information about the first to third sections to the mode controller 153. The mode controller 153 may receive the current location from the location obtainer 155 and control the display mode based on to which section the current location belongs. For example, the third mode that is a general mode may be selected in the first section that is an initial section, the second mode may be selected in the second section that is a middle section so as to prevent sleepiness, and the first mode may be selected in the third section that is a last section for deep sleep.

However, the mode controller 153 may override the display mode by considering the sleepiness of the driver, which is determined by the sleepiness determiner 152, rather than information about the first to third sections. In other words, even when the display mode is controlled based on sections, the display mode may be set to the second mode when the driver is determined to be sleepy.

The output signal generator 154 generates an output signal for displaying an image on the display panel 110 based on the display mode. The output signal generator 154 obtains an external image signal and processes the external image signal according to the display mode to generate the output signal. The output signal generated by the output signal generator 154 may be provided to the controller 140.

The output signal generator 154 may process the external image signal according to the display mode. When the display mode is the third mode, the display panel 110 uses all blue sub-pixels, and thus, the external image signal may be transmitted intact to the controller 140. However, when the display mode is the first or second mode, the display panel 110 uses the first or second sub-pixels from among the two types of blue sub-pixels, and thus, the external image signal needs to be processed.

For example, the output signal generator 154 may set a pixel value corresponding to the first blue sub-pixel to be 0 in the first mode and set a pixel value corresponding to the second blue sub-pixel to be 0 in the second mode to generate the output signal. The output signal generator 154 may split a pixel value originally assigned to a pixel that is changed to 0 to pixels adjacent to the pixel. For example, when a blue pixel value of a certain pixel including the first blue sub-pixel is changed to 0, the blue pixel value assigned to the certain pixel in an original image may be distributed to pixels including the second blue sub-pixel from among adjacent pixels of the certain pixel. Accordingly, blue pixel values of the adjacent pixels of the certain pixel may increase.

Figure 4:
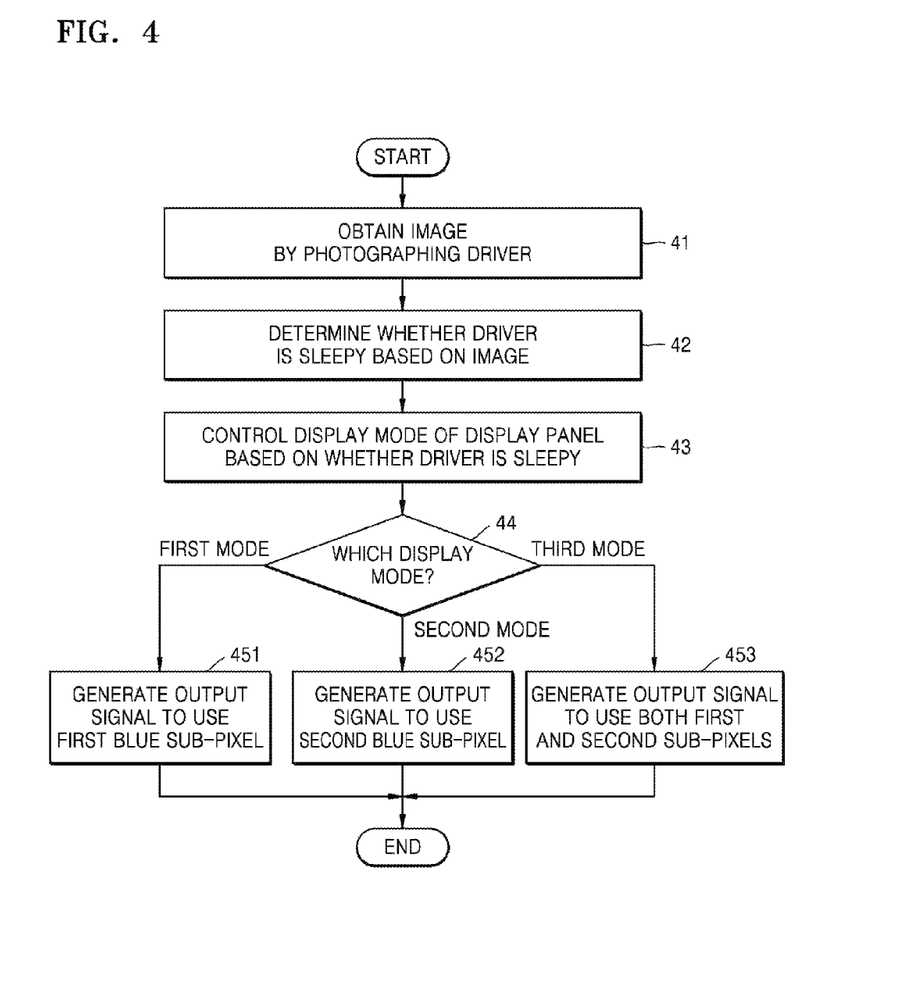
FIG. 4 is a flowchart of a display control method according to an exemplary embodiment.

FIG. 4 is a flowchart of a display control method according to an exemplary embodiment.

The method of FIG. 4 includes operations that are repeatedly processed in a time series by the display control apparatus 150 of FIG. 3. Accordingly, descriptions provided above with reference to FIG. 3 apply the method of FIG. 4 even though omitted. Hereinafter, the method of FIG. 4 will be described with reference to the components of FIG. 3. In FIG. 4, the viewer is referred to as a driver, but embodiments are not limited thereto and may be applied to any viewer.

Referring to FIG. 4, in operation 41, the image obtainer 151 obtains an image by photographing the driver.

In operation 42, the sleepiness determiner 152 determines whether the driver is sleepy based on the image obtained in operation 41.

In operation 43, the mode controller 153 controls the display mode of the display panel 110 based on whether the driver is sleepy.

In operation 44, the output signal generator 154 performs one of operations 451, 452, or 453 based on the display mode to generate the output signal. When the display mode is the first mode, operation 451 is performed so that the output signal generator 154 generates the output signal to use the first blue sub-pixel, and when the display mode is the second mode, operation 452 is performed so that the output signal generator 154 generates the output signal to use the second blue sub-pixel. When the display mode is the third mode, operation 453 is performed so that the output signal generator 154 generates the output signal to use both the first and second blue sub-pixels.

Figure 5A:
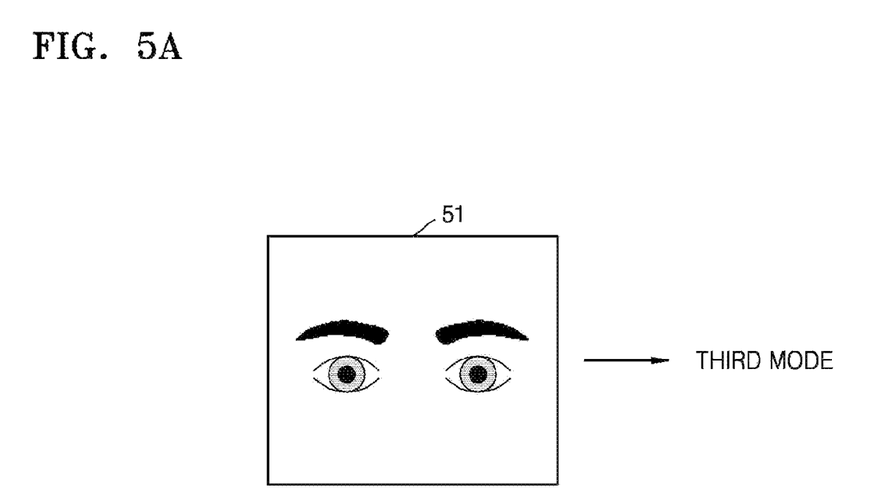
FIG. 5A and FIG. B are diagrams for describing a method of controlling a display mode, according to an exemplary embodiment.
Figure 5B:
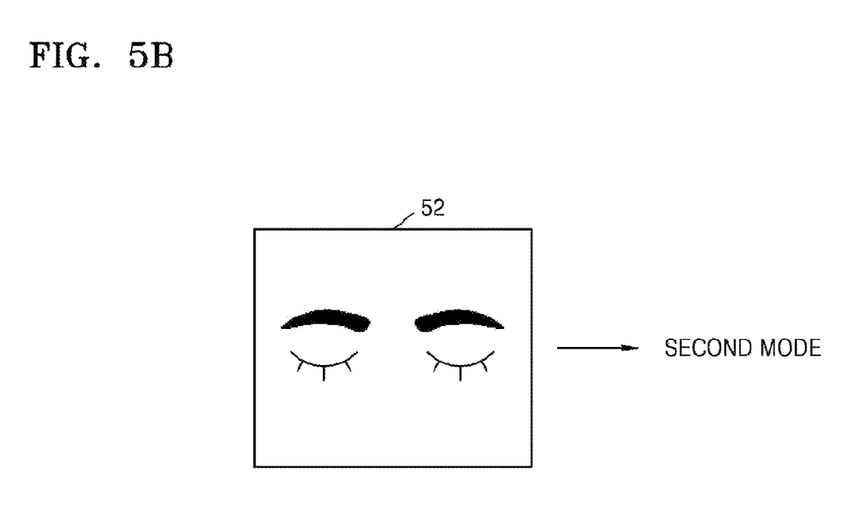

FIG. 5A and FIG. 5B are diagrams for describing a method of controlling a display mode according to an exemplary embodiment.

Referring to FIG. 5A and FIG. 5B, images 51 and 52 obtained by photographing a viewer and display modes according to the images are shown. First, in FIG. 5A, the image 51 shows the viewer with opened eyes. At this time, the sleepiness determiner 152 determines that the viewer is not sleepy and the mode controller 153 may select the third mode.

In FIG. 5B, the image 52 shows the viewer with closed eyes. At this time, when the duration of the eyes being closed continues at least for a certain period of time, for example, at least 1 second, the sleepiness determiner 152 may determine that the viewer is sleepy and the mode controller 153 may select the second mode.

Figure 6:
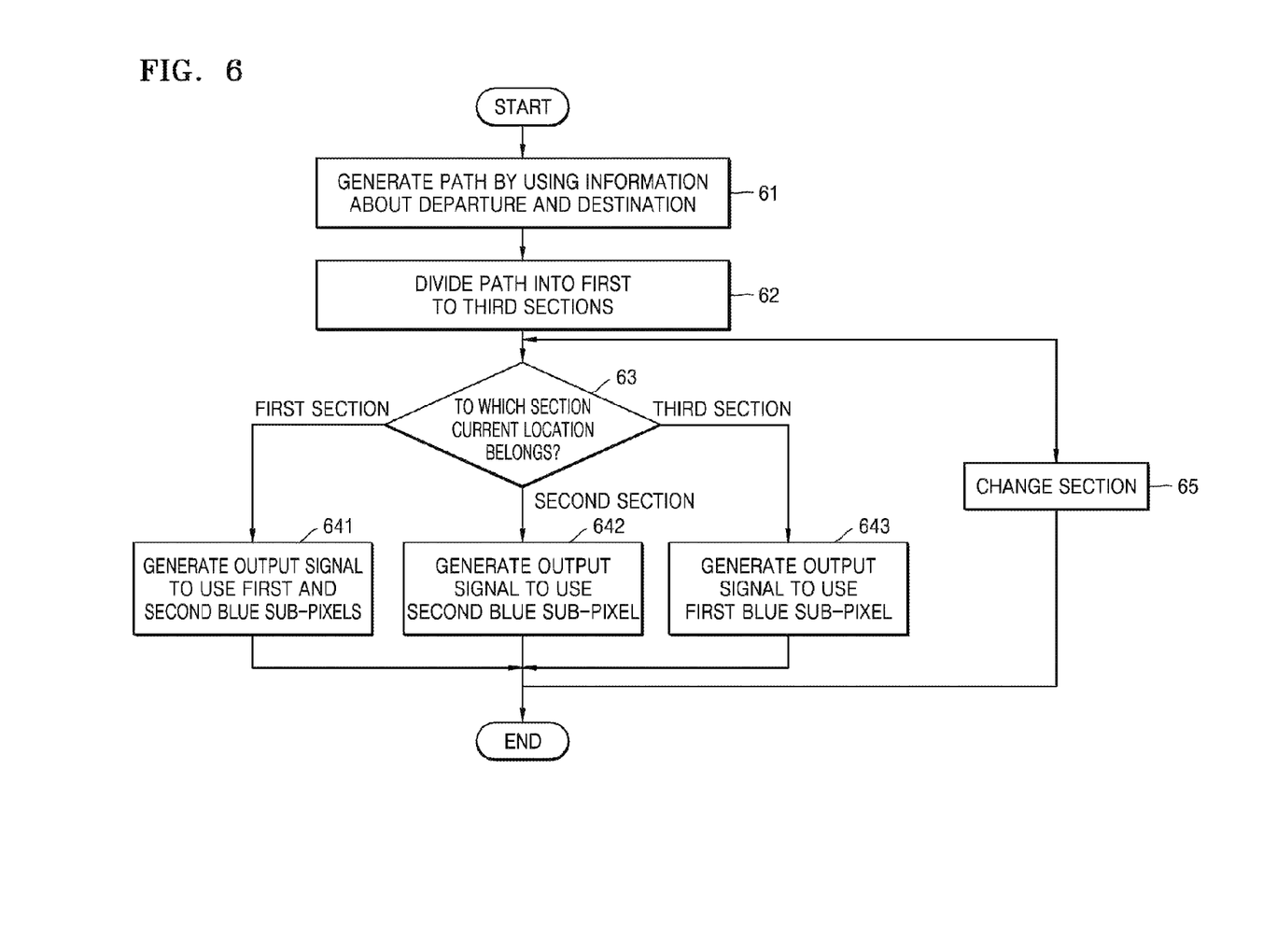
FIG. 6 is a flowchart of a display control method according to another exemplary embodiment.

FIG. 6 is a flowchart of a display control method according to an exemplary embodiment.

The method of FIG. 6 includes operations that are processed in a time series by the display control apparatus 150 of FIG. 3. Accordingly, descriptions provided above with reference to FIG. 3 apply the method of FIG. 6 even though omitted. Hereinafter, the method of FIG. 6 will be described with reference to the components of FIG. 3.

Referring to FIG. 6, in operation 61, the location obtainer 155 generates a path by using information about a departure and a destination.

In operation 62, the location obtainer 155 divides the path into first, second, and third sections.

In operation 63, the mode controller 153 controls the display mode by determining to which section a current location belongs. When the current location is in the first section, the mode controller 153 selects the third mode that is a general mode to perform operation 641. When the current location is in the second section, the mode controller 153 selects the second mode that is a wake-up mode to perform operation 642. When the current location is in the third section, the mode controller 153 selects the first mode that is a sleep inducing mode to perform operation 643.

In operation 641, the output signal generator 154 generates an output signal to use the first and second blue sub-pixels. In operation 642, the output signal generator 154 generates an output signal to use the second blue sub-pixel. In operation 643, the output signal generator 154 generates an output signal to use the first blue sub-pixel.

In operation 65, the mode controller 153 continuously obtains a location from the location obtainer 155 and performs operation 63 when a section of the obtained location changes.

Figure 7:
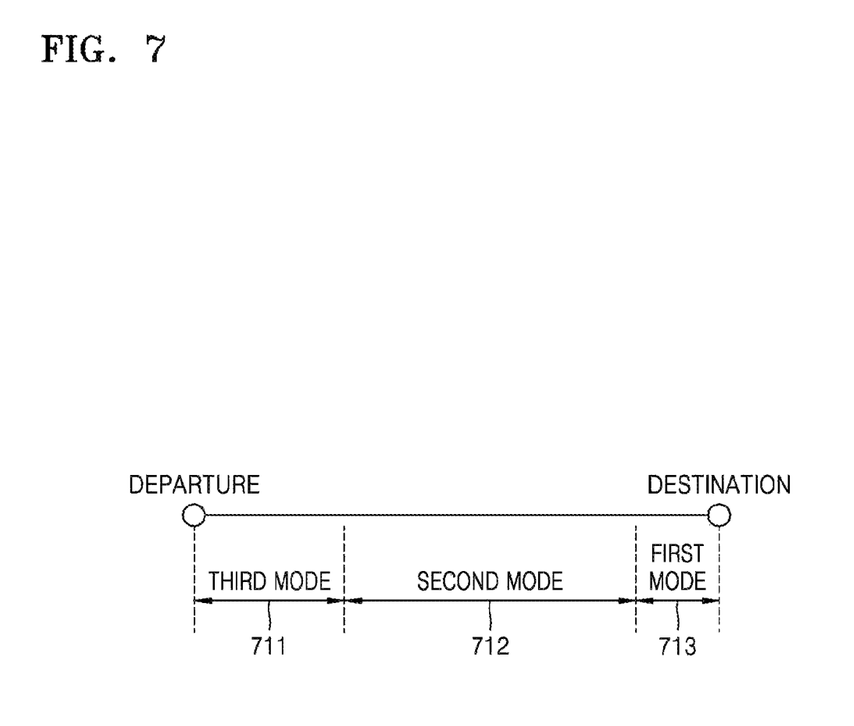
FIG. 7 is a diagram of a path according to an exemplary embodiment.

FIG. 7 is a diagram of a path according to an exemplary embodiment (again, with reference to the apparatus of FIG. 3).

Referring to FIG. 7, the location obtainer 155 may generate a path from a departure location to a destination location and divide the path into a first section 711, a second section 712, and a third section 713. The mode controller 153 changes a display mode when entering each section. For example, the mode controller 153 may select the third mode in the first section 711, the second mode in the second section 712, and the first mode in the third section 713.

A display apparatus according to one or more exemplary embodiments described above provides a sleep inducing effect or a wake-up effect to a viewer, and thus, the display apparatus may be useful when the sleep inducing effect or the wake-up effect is required. For example, the display apparatus may used for learning and may provide the wake-up effect to a learner. Alternatively, the display apparatus may be used for a car to provide a screen to a driver and may provide the wake-up effect to the driver. The display apparatus may be used in other various situations.

A display apparatus and a display control method and apparatus according to one or more exemplary embodiments provide a function of inducing a user to wake up or fall asleep.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. A display control method for controlling display of a display panel, the display control method comprising:
   obtaining an image of a viewer;
   determining whether the viewer is sleepy based on the obtained image;
   controlling a display mode of the display panel based on the determination of whether the viewer is sleepy; and
   generating an output signal for displaying an image on the display panel based on the display mode,
   wherein the display panel comprises a first blue pixel emitting a first blue light and a second blue pixel emitting a second blue light having a different wavelength from the first blue light, and the display mode being classified based on which of the first and second blue pixels are emitting during the display mode, and further comprising:
   generating a path using information about a departure location and a destination location;
   dividing the path into a first section, a second section, and a third section in the stated order from the departure location to the destination location, and
   wherein the controlling comprises controlling the display mode by selecting the display mode when entering each of the first to third sections.

2. The display control method of claim 1, wherein the controlling comprises selecting one of a first mode displaying an image by using the first blue pixel, a second mode displaying an image by using the second blue pixel, and a third mode displaying an image by using both the first and second blue pixels,
   wherein the third mode is selected in the first section, the second mode is selected in the second section, and the first mode is selected in the third section.

3. The display control method of claim 1, wherein the controlling comprises overriding the display mode based upon whether the viewer is sleepy.

4. The display control method of claim 1, wherein a wavelength of the first blue light is shorter than that of the second blue light.

5. The display control method of claim 4, wherein a center wavelength of the first blue light is in a range from about 440 nm to about 450 nm, and a center wavelength of the second blue light is in a range from about 460 nm to about 470 nm.

6. The display control method of claim 1, wherein the determining comprises determining whether the eyes of the viewer are closed, and when a duration of the eyes being closed is higher than a pre-set reference value, determining that the viewer is sleepy.

7. The display control method of claim 1, wherein obtaining the image of the viewer comprises photographing the viewer.

8. A display control apparatus for controlling display of a display panel, the display control apparatus comprising:
   an image obtainer that obtains an image of a viewer;
   a sleepiness determiner that determines whether the viewer is sleepy based on obtained the image;
   a mode controller that controls a display mode of the display panel based on determining whether the viewer is sleepy;
   a location obtainer determiner that generates a path by using information about a departure location and a destination location, and
   divides the path into a first section, a second section, and a third section in the stated order from the departure location to the destination location; and
   an output signal generator that generates an output signal for displaying an image on the display panel based on the display mode,
   wherein the display panel comprises a first blue pixel emitting a first blue light and a second blue pixel emitting a second blue light having a different wavelength from the first blue light, and
   the display mode being classified based on which of the first and second blue pixels are emitting during the display mode, and wherein the display mode controller further controls the display mode by selecting the display mode when entering each of the first to third sections.

9. The display control apparatus of claim 8, wherein the image obtainer obtains a photograph of the viewer.

10. The display control apparatus of claim 8, wherein the first blue pixel and the second blue pixel are sub-pixels of a pixel that includes a single red sub-pixel and a single green sub-pixel.

11. The display control apparatus of claim 8, wherein a center wavelength of the first blue light emitted by the first blue pixel is in a range from about 440 nm to about 450 nm, and a center wavelength of the second blue light emitted by the second blue pixel is in a range from about 460 nm to about 470 nm.

12. A non-transitory computer-readable medium having stored thereon instructions, which when executed by a computer, performs display control operations comprising:
   obtaining an image of a viewer;
   determining whether the viewer is sleepy based on the obtained image;
   controlling a display mode of a display panel based on the determination of whether the viewer is sleepy; and
   generating an output signal for displaying an image on the display panel based on the display mode,
   wherein the display panel comprises a first blue pixel emitting a first blue light and a second blue pixel emitting a second blue light having a different wavelength from the first blue light, and
   the display mode being classified based on which of the first and second blue pixels are emitting during the display mode, and further comprising instructions for performing operations comprising:
   generating a path using information about a departure location and a destination location; and
   dividing the path into a first section, a second section, and a third section in the stated order from the departure location to the destination location, wherein the controlling operations comprise controlling the display mode by selecting the display mode when entering each of the first to third sections.

13. The non-transitory computer-readable medium of claim 12, wherein instructions for performing controlling operations comprise instructions for performing operations comprising:
   selecting one of:
      a first mode displaying an image by using the first blue pixel,
      a second mode displaying an image by using the second blue pixel, and
      a third mode displaying an image by using both the first and second blue pixels,
   wherein the third mode is selected in the first section, the second mode is selected in the second section, and the first mode is selected in the third section.

14. The non-transitory computer-readable medium of claim 12, further comprising instructions for performing operations comprising selecting one of:
   a first mode displaying an image by using the first blue pixel;
   a second mode displaying an image by using the second blue pixel; and
   a third mode displaying an image by using both the first and second blue pixels.

15. The non-transitory computer-readable medium of claim 14, further comprising instructions for performing operations comprising:
   selecting the second mode when it is determined that the viewer is sleepy; and
   selecting the third mode when it is determined that the viewer is not sleepy.

* * * * *